US009139611B2

(12) United States Patent
Johnson et al.

(10) Patent No.: US 9,139,611 B2
(45) Date of Patent: Sep. 22, 2015

(54) PROCESS FOR PREPARING PARTICLES OF PROTEINACEOUS MATERIAL

(75) Inventors: Richard Alan Johnson, Nottingham (GB); John Rodney Woodrow, Nottingham (GB)

(73) Assignees: NOVOZYMES BIOPHARMA DK A/S, Bagsvaerd (DK); UPPERTON LIMITED, Nottingham (GB)

( * ) Notice: Subject to any disclaimer, the term of this patent is extended or adjusted under 35 U.S.C. 154(b) by 1264 days.

(21) Appl. No.: 12/373,176

(22) PCT Filed: Jul. 13, 2007

(86) PCT No.: PCT/GB2007/050402
§ 371 (c)(1),
(2), (4) Date: Jan. 9, 2009

(87) PCT Pub. No.: WO2008/007146
PCT Pub. Date: Jan. 17, 2006

(65) Prior Publication Data
US 2009/0197316 A1 Aug. 6, 2009

(30) Foreign Application Priority Data

Jul. 13, 2006 (GB) .................................. 0613884.6
Feb. 1, 2007 (GB) .................................. 0701925.0

(51) Int. Cl.
| | | |
|---|---|---|
| C07K 17/00 | (2006.01) | |
| C07K 1/02 | (2006.01) | |
| A61K 9/16 | (2006.01) | |
| A61K 9/51 | (2006.01) | |
| A61K 47/48 | (2006.01) | |
| A61K 49/04 | (2006.01) | |
| A61K 49/08 | (2006.01) | |
| A61K 49/14 | (2006.01) | |
| A61K 49/18 | (2006.01) | |
| A61K 51/08 | (2006.01) | |
| A61K 51/12 | (2006.01) | |
| B82Y 5/00 | (2011.01) | |
| C07K 1/08 | (2006.01) | |
| C07K 1/10 | (2006.01) | |

(52) U.S. Cl.
CPC ................ *C07K 1/02* (2013.01); *A61K 9/1658* (2013.01); *A61K 9/5169* (2013.01); *A61K 47/483* (2013.01); *A61K 47/48246* (2013.01); *A61K 47/48284* (2013.01); *A61K 47/48292* (2013.01); *A61K 47/48884* (2013.01); *A61K 49/0485* (2013.01); *A61K 49/085* (2013.01); *A61K 49/143* (2013.01); *A61K 49/1881* (2013.01); *A61K 51/081* (2013.01); *A61K 51/1255* (2013.01); *B82Y 5/00* (2013.01); *C07K 1/08* (2013.01); *C07K 1/10* (2013.01)

(58) Field of Classification Search
None
See application file for complete search history.

(56) References Cited

U.S. PATENT DOCUMENTS

| | | | |
|---|---|---|---|
| 6,458,387 B1 * | 10/2002 | Scott et al. | 424/489 |
| 2003/0171267 A1 | 9/2003 | Sadeghi et al. | |
| 2005/0036946 A1 * | 2/2005 | Pathak et al. | 424/9.4 |

FOREIGN PATENT DOCUMENTS

| | | |
|---|---|---|
| EP | 1683517 | 7/2006 |
| WO | 90/13653 A1 | 11/1990 |
| WO | 96/37515 A1 | 11/1996 |
| WO | WO 97/36614 | 10/1997 |
| WO | 98/46732 A1 | 10/1998 |
| WO | 00/44772 A2 | 8/2000 |
| WO | WO00/67774 | 11/2000 |
| WO | WO 01/45761 | 6/2001 |
| WO | WO 03/018613 | 3/2003 |
| WO | 2004/020405 A2 | 3/2004 |
| WO | 2004/020454 A2 | 3/2004 |
| WO | 2006/000071 A1 | 1/2006 |
| WO | 2006/096515 A2 | 9/2006 |

OTHER PUBLICATIONS

"Isovue", Drug Information Online Drugs.com, pp. 1-4 of 21, downloaded on Mar. 7, 2012 from http://www.drugs.com/pro/isovue.html.*
Hermanson et al., Bioconjugate Techniques, pp. 169-186 (1996).
Macgillivray et al., Molecular and Cellular Iron Transport, pp. 41-69 (2002).
Mason et al., Biochemistry, vol. 32, pp. 5472-5479 (1993).
Kruip et al., "Structural Organisation of the Major Subunits in Cyanobacterial Photosystem 1", Journal of Biological Chemistry, vol. 272, No. 27, pp. 17061-17069 (1997).
Winkelhake et al., "Protracted Circulating Lifetimes of Mannose-terminated Glycoproteins and Aggregated Albumin in Mice Infected With LDH-elevating Virus", Physiological Chemistry and Physics, vol. 10, pp. 305-322 (1978).
International Search Report for PCT/GB2007/050402 dated Oct. 25, 2007.

* cited by examiner

*Primary Examiner* — Yunsoo Kim
(74) *Attorney, Agent, or Firm* — Michael W. Krenicky

(57) ABSTRACT

Protein particles are prepared by causing or allowing protein molecules dispersed in a liquid medium at a concentration of 8 mg.mL−1 or greater to react in the presence of a zero-length crosslinker, so as to produce protein particles comprising protein molecules that are covalently bonded together. The protein particles may be produced with sizes in the sub-micron range with closely defined sizes and size distributions. The particles have applications in many fields, but are useful inter alia for the delivery of therapeutic agents and other agents, eg imaging contrast agents, to the body.

33 Claims, 11 Drawing Sheets a) 0mM EDC b) 15mM EDC c) 30mM EDC d) 45mM EDC e) 15mM EDC + 5mM NHS a) Crosslinked product b) Desalted product c) Formulated product d) Freeze dried product 15mM EDC + 5mM NHS
Pre heat treatment Collected product 15mM EDC + 5mM NHS
Post heat treatment

PROCESS FOR PREPARING PARTICLES OF PROTEINACEOUS MATERIAL

CROSS-REFERENCE TO RELATED APPLICATIONS

This application is a 35 U.S.C. 371 national application of PCT/GB2007/050402 filed Jul. 13, 2007, which claims priority or the benefit under 35 U.S.C. 119 of Great Britain application nos. 0613884.6 and 0701925.0 filed Jul. 13, 2006 and Feb. 1, 2007, respectively, the contents of which are fully incorporated herein by reference.

FIELD OF THE INVENTION

This invention relates to a process for preparing particles of proteinaceous material, and to particles of proteinaceous material having defined size ranges. The invention also relates to the use of particles of proteinaceous material for the delivery of agents, eg to the body. Such agents may be therapeutic agents or imaging contrast agents for use in medical imaging techniques. For instance, the particles may be labelled with radioactive isotopes for use in medical imaging, eg bone marrow and lymphatic scanning. The proteinaceous material itself may have a therapeutic benefit, in which case the formation of particles in accordance with the invention may result in enhanced delivery or extended residence time of the proteinaceous material in the body.

BACKGROUND OF THE INVENTION

The use of colloidal materials for investigating the functionality of the lymphatic system is well known. Radioactive nanocolloids are used in nuclear medicine for bone marrow scanning, inflammation imaging and investigating lymphatic drainage, including the identification of the 'sentinel node' in investigations of metastatic spread of some cancers. Only a limited number of commercial products are currently available, including technetium-99m ($^{99m}$Tc) colloidal albumin formulations (eg those sold under the trade names NANO-COLL, in which 95% of the particles have a diameter of ≤80 nm, and ALBURES, in which the mean particle size is stated to be 500 nm) and various sulphur colloids labelled with $^{99m}$Tc.

It is thought that the differences in particle size and particle size distribution between current formulations are fundamental to the differences exhibited in vivo, eg uptake, biodistribution and clearance. For example, particle size will influence the efficiency with which the particles are engulfed by lymph nodes. Thus, it is desirable for particles with sizes in the sub-micron range (nanoparticles) to be produced with closely defined sizes and size distributions.

It is therefore an object of the invention to provide improved methods for the preparation of nanoparticles having closely defined mean particle sizes and size distributions. Such particles may be useful inter alia for the delivery of therapeutic or other agents to the body, eg when conjugated to a radiopharmaceutical for use in nuclear imaging applications, or to prolong the residence time of proteinaceous material in the body.

It is known that protein particles may be coupled together using so-called zero-length crosslinkers. Such chemistry is disclosed in, for instance, US-A-2005/0036946, which describes the cross-linking of chemically-modified albumin to form solid-like gels. WO-A-00/67774 describes the cross-linking of unspecified mixtures of proteins. Prior to cross-linking the proteins are rendered insoluble and denatured by acidification, addition of non-aqueous solvent and heating to elevated temperature. The product can be recovered by low speed centrifugation and homogenisation is required to allow injection, which indicates that the product is insoluble, with rather large particle sizes. Likewise, WO-A-97/36614 discloses the cross-linking of Protein A at a concentration of 4 mg.mL$^{-1}$. Similarly, Winkelhake et al, *Physiol Chem & Phys* 10 (1978), 305-322 describes cross-linking of bovine serum albumin at a concentration of 5 mg.mL$^{-1}$. The cross-linking of albumin is also described in WO-A-01/45761, the product being used as a sealant, which shows that the product must have the form of a macroscopic solid structure.

SUMMARY OF THE INVENTION

The inventor has found for the first time that the use of zero-length crosslinkers at higher concentrations of protein than those disclosed in the prior art leads to the formation of protein nanoparticles, and that by appropriate control of the reaction conditions the average particle size and the size distribution of the resulting particles can be closely controlled.

According to a first aspect of the invention, there is provided a process for the preparation of protein particles, which process comprises causing or allowing protein molecules dispersed in a liquid medium at a concentration of 8 mg.mL$^{-1}$ or greater to react in the presence of a zero-length crosslinker, so as to produce protein particles comprising protein molecules that are covalently bonded together.

By "particle" is meant a conjugate or agglomerate comprising a plurality of protein molecules that are covalently bonded to each other. The particles may exist as a discernible discrete phase when dispersed in a suitable medium, or their presence in the medium may not be visible to the naked eye, in which case the particles may be regarded as soluble particles. The term particle is thus intended to encompass both solid-like particles and particles that exist in a form akin to a classical solution.

By "zero-length crosslinker" is meant a compound which promotes the reaction of groups on the protein molecules without any chemical moiety or "spacer" being interposed between those groups.

The protein molecules that are covalently bound together in the process of the invention are most preferably molecules of a single protein. Alternatively, the protein particles may be formed from mixtures of two or more different proteins.

The process of the invention is carried out in a suitable medium, which is most commonly an aqueous medium. Preferably the medium will be a buffer solution, and the process thus involves dispersing the protein molecules and zero-length crosslinker in buffer solution.

The product is generally purified following reaction of the protein molecules and zero-length crosslinker. Purification typically involves removal of the excess reagents, which may be carried out using any known method, eg column chromatography. A heat treatment step may also be included to hydrolyse any bound crosslinker, and the released species may then be removed by known methods, eg column chromatography.

The process according to the invention is advantageous because the reaction conditions can be controlled in such a way that the mean size of the protein particles may be controlled. In addition, the width of the particle size distribution may be relatively narrow, leading to a relatively high degree of uniformity in the properties of the particles.

One suitable method for the determination of particle size is light scattering, and references to particle size herein should be understood to refer to particle size as measured by such a method. For instance, the particle size may be determined using a Malvern Zetasizer Nano S (supplied by Malvern Instruments Ltd, Enigma Business Park, Grovewood Road, Malvern, Worcestershire WR14 1XZ, United Kingdom). The data generated by such an instrument is most conveniently expressed in terms of the intensity of scattered light as a function of particle size. The mean particle size and standard deviation may be calculated automatically using dedicated software supplied by the manufacturer.

In a measurement of particle size distribution, a peak may be defined as $\{X(i), Y(i); i=i1 \ldots i2\}$ where $Y(i)$ is the % intensity in size class i, and $X(i)$ is the size class. The total area under the curve, the mean particle size ($\mu$) and the standard deviation ($\sigma$) are as follows:—

$$\text{Area} = \sum_{i=i_1}^{i_2} Y(i)$$

$$\mu = \frac{\sum_{i_1}^{i_2} X(i) * Y(i)}{\text{Area}}$$

$$\sigma = \sqrt{\frac{\sum_{i_1}^{i_2} X(i)^2 Y(i)}{\text{Area}} - \mu^2}$$

Thus, according to a second aspect of the invention, there are provided protein particles comprising protein molecules that are directly coupled together, by covalent linkages between functional groups on the protein molecules, and wherein the protein particles have a mean particle size of less than 200 nm, more preferably less than 150 nm, or less than 100 nm, 80 nm, 50 nm, 40 nm, 30 nm or 20 nm. Preferably, the standard deviation of the particle size distribution is less than 100%, or less than 80% or less than 60%, of the mean particle size. The standard deviation of the particle size may be less than 50%, or less than 40%, of the mean particle size.

The particles according to the invention may have a mean particle size of more than 5 µm, or more than 10 µm, 20 µm, 30 µm, 40 µm, 50 µm, 70 µm or more than 100 µm.

Particular mean particle size ranges that may be mentioned are (a) for smaller particles, 5 nm to 50 nm, or 10 nm to 40 nm, 10 nm to 30 nm, or 10 nm to 20 nm; (b) for mid-sized particles, 10 nm to 100 nm, or 20 nm to 80 nm, or 20 nm to 50 nm; and (c) for larger particles, 50 nm to 200 nm, or 50 nm to 150 nm, or 50 nm to 130 nm.

Nanoparticles of smaller particle size than 200 nm, and in particular those with mean particle sizes of less than 130 µm, are of particular utility in that they may be sterilised by 0.2 µm filtration. This has important benefits in manufacturing and processing terms in that it permits simple sterilisation without significant loss of material.

It is particularly preferred that the particles in accordance with the invention should be free, or substantially free, of material other than the protein molecules from which the particle is formed and any therapeutic or other agents to which the particles are physically or chemically bound. In particular, as the particles comprise residues of protein molecules that are directly coupled together, by covalent linkages between functional groups on the protein molecules themselves, the particles do not comprise intermediate linking or spacer groups derived from crosslinking agents or the like.

In addition, the process according to the invention is simple, involving a single phase reaction for which no solvent or surfactant is required. The mean size of the particles may easily be varied by adjustment of a small number of variables, the mean size and size distribution being reproducible under set reaction conditions. Furthermore, the simplicity of the process facilitates scale-up. The process of the invention is additionally advantageous in that the zero-length nature of the crosslinking agent means that the particles do not contain a synthetic spacer. The presence of additional components, or residues of additional components, which are of no therapeutic or functional benefit, and which could be harmful, is therefore avoided.

Amongst other applications, the protein particles of the present invention have particular utility in medical imaging applications, when conjugated to an imaging contrast agent.

Thus, according to a further aspect of the invention there is provided a conjugate for use in medical imaging, which conjugate comprises a protein particle formed by the process of the first aspect of the invention, or a protein particle according to the second aspect of the invention, conjugated to an imaging contrast agent, or a precursor thereof.

By "medical imaging" is meant any technique used to visualise an internal region of the human or animal body, for the purposes of diagnosis, research or therapeutic treatment. Such techniques include principally X-ray imaging, magnetic resonance imaging (MRI), nuclear imaging, and positron emission tomography (PET), and also ultrasound techniques, though the last-named is of lesser significance in relation to the present invention. Agents useful in enhancing such techniques are those materials that enable visualisation of a particular locus, organ or disease site within the body, and/or that lead to some improvement in the quality of the images generated by the imaging techniques, providing improved or easier interpretation of those images. Such agents are referred to herein as imaging contrast agents, the use of which facilitates the differentiation of different parts of the image, by increasing the "contrast" between those different regions of the image. The term "imaging contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging).

By a "precursor" of an imaging contrast agent is meant a moiety that is not in itself effective as an imaging contrast agent but which can be rendered so effective by reaction or admixture with some other species prior to use. An example of such a precursor is a metal-chelating moiety, capable of forming physical bonds with metal ions so as to form a metal chelate that functions as an imaging contrast agent.

MRI contrast agents that may be employed in the invention include metal ions, notably gadolinium. Such ions may be coupled to the protein particles via a chelating moiety that is covalently bound to the protein particles.

Similarly, metals useful in nuclear imaging, eg $^{99m}$Tc, $^{201}$Tl and $^{111}$In, may also be coupled to the carrier material, either directly or indirectly, eg via a chelating moiety. Labelling with sodium pertechnetate ($^{99m}$Tc) is particularly useful for bone marrow scanning and inflammation scanning applications, and in particular for scanning of the lymphatic system.

In a similar manner, the protein particles of the present invention may be used to deliver other agents to the body, such as therapeutic agents.

Thus, according to a yet further aspect of the invention there is provided a conjugate comprising a protein particle formed by the process of the first aspect of the invention, or a protein particle according to the second aspect of the invention, conjugated to a therapeutic agent.

The particles or conjugates according to the invention will generally be administered to the body as a formulation comprising a pharmaceutically acceptable liquid medium. That medium will generally be an aqueous medium, most commonly an aqueous medium containing appropriate excipients. Such excipients may include one or more tonicity-adjusting agents, preservatives, surfactants, and other conventional pharmaceutical excipients.

Thus, according to another aspect of the invention there is provided a formulation comprising protein conjugates as defined above, in admixture with a pharmaceutically acceptable liquid medium.

DETAILED DESCRIPTION OF THE INVENTION

Nature of the Protein

Proteins that may be used in the process according to the invention include globular proteins and fibrous or structural proteins.

The protein is most preferably a single, complete or substantially complete, protein molecule.

The protein molecule may alternatively be a fragment of a complete protein molecule, by which is meant a molecule comprising a sequence of amino acids that corresponds to a sequence of amino acids found in a naturally-occurring protein molecule, but which is shorter in length. Such a fragment, however, preferably comprises a sequence of amino acids that has a length of more than 20%, 30%, 40%, 50%, 60%, 70%, 80%, or 90% and most preferably more than 95% that of a naturally-occurring protein molecule, and which has a degree of homology of greater than 80%, 90% or most preferably greater than 95% with the corresponding part of the naturally-occurring protein molecule.

The protein molecule may also be a derivative or mutant of a naturally occurring protein.

Examples of globular proteins include synthetic or natural serum proteins, as well as salts and natural or synthetic derivatives thereof (eg enzymatically, chemically, or otherwise modified, cleaved, shortened or crosslinked, oxidised or hydrolysed derivatives or subunits thereof). Examples of fibrous or structural proteins include synthetic or natural collagen, elastin, keratin, fibroin, fibrin, and fibronectin, and natural or synthetic derivatives thereof. Examples of serum proteins are albumin, transthyretin, fibrinogen, thrombin and transferrin. Other proteins that may be mentioned include apolipoprotein A-1, lactoferrin and antibodies. The proteins may also be fusion proteins, ie recombinant products comprising a first protein (or fragment or variant thereof), eg human serum albumin, fused to another protein or polypeptide (or fragment or variant thereof). Fusion proteins are normally prepared by recombinant methods, using contiguous DNA that encodes the first protein and the other protein or polypeptide. Examples of albumin fusion proteins are disclosed in WO-A-90/13653, WO-A-01/79271 and WO-A-060071, the teaching of each of which is hereby incorporated by reference. Examples of transferrin fusion proteins are disclosed in WO-A-2004/020454, WO-A-2004/020405 and WO-A-2006/096515, the teaching of each of which is hereby incorporated by reference.

A particularly preferred protein for use in the process of the present invention is albumin, for the reasons detailed below.

Where the conjugates are intended for administration to the human body, the protein is preferably of human origin, ie actually derived from humans, or is identical (or substantially so) in structure to protein of human origin. A particularly preferred protein is thus human serum albumin. For certain applications, non-human albumin may be used, especially mammalian albumins, eg bovine serum albumin, horse serum albumin and dog serum albumin.

Human serum albumin may be serum-derived, for instance obtained from donated blood. However, in order to eliminate or reduce the risk of transmission of potential contaminants (eg viral or other harmful agents, that may be present in blood-derived products), as well as the potential limitations on supply associated with material isolated from donated blood, it is preferred that the protein, eg human serum albumin, should be a recombinant product. Such a recombinant protein may be derived from microorganisms (including cell lines) or from transgenic plants or animals that have been transformed or transfected to express the protein.

The presently most-preferred protein for use in the present invention is thus recombinant human serum albumin (rHA). Suitable forms of rHA may be obtained commercially from Novozymes Delta Ltd, Nottingham, United Kingdom.

Processes for the preparation of rHA will in general be familiar to those skilled in the art and are described, for instance, in WO 96/37515 and WO 00/44772.

In a preferred process for the preparation of rHA, an rHA solution is derived from a fungal culture medium obtained by culturing a fungus transformed with an rHA-encoding nucleotide sequence in a fermentation medium. The fungus expresses rHA and secretes it into the medium. Appropriate purification of the culture supernatant may then yield a suitable solution for use in the process of the invention. The fungus may be a filamentous fungus such as an *Aspergillus* species. Preferably, the fungus is a yeast. More preferably, the fungus is of the genus *Saccharomyces* (eg *S. cerevisiae*), the genus *Kluyveromyces* (eg *K. lactis*) or the genus *Pichia* (eg *P. pastoris*).

The rHA preferably contains a substantial proportion of molecules with a free SH (sulphydryl or thiol) group. This provides a particularly useful means of conjugation of the rHA molecule to a therapeutic agent or imaging contrast agent, as described below.

Albumin is the currently preferred protein for the preparation of protein particles according to the process of the present invention, for the following reasons:
a) albumin is highly soluble in aqueous media;
b) the free sulphydryl group present in the albumin molecule provides a means for selective coupling to a therapeutic agent or imaging contrast agent;
c) the numerous amino acid residues with pendant amino groups (specifically lysine residues), and also the large number of carboxyl groups, present in the albumin molecule provide for efficient covalent bonding between albumin molecules through the formation of amide bond; and
d) the numerous amino acid residues with pendant amino groups and the relatively large number of carboxyl groups are also useful in providing coupling sites for agents for delivery to the body.

Other proteins that may usefully be employed in the present invention are those that are normally rapidly cleared from the bloodstream due to excretion via the kidney. The formation of protein particles of the invention may increase the in vivo half-life of such proteins.

For example, the naturally occurring apolipoprotein A-1 (Apo A-1), which is the major protein component of High Density Lipoprotein (HDL) (so-called "good cholesterol"), is such a protein.

Plasma levels of the Apo A-1 lipoprotein are reduced in patients with atherosclerosis. When atherosclerosis patients are treated with dimerised Apo A-1 (to extend its blood pool residence) their levels of plaque reduce significantly, with a corresponding drop in the rates of heart attack.

Intravenous administration of Apo A-1 has been attempted previously but the protein is rapidly cleared from the blood pool as it is relatively small and is secreted from the kidney via glomerular filtration, appearing in the urine shortly after injection.

By the methodology of the present invention, it is possible to make a higher molecular weight nanoparticle that is too large to be excreted from the blood through the kidney, thereby extending the half-life of this important plasma protein. For similar reasons to albumin, apolipoprotein A-1 used in the invention is preferably a recombinant product.

Another protein that may be useful in the invention is transferrin. The use of transferrin may be beneficial for some applications because it has numerous potential coupling sites, it may facilitate transport across the blood-brain barrier, and it may be prepared as a recombinant product (see, for example, MacGillivray et al 2002, *in Molecular and Cellular Iron Transport*, Templeton (*Ed*), Marcel Dekker, Inc, p 41 and Mason et al 1993, *Biochemistry* 32: 5472). As for albumin, transferrin is preferably recombinant transferrin (rTF).

As mentioned above, other proteins that may be useful in the invention include lactoferrin and antibodies. These too may be recombinant products.

The description of the various parameters and reaction conditions given below is applicable to albumin, but may also be applicable to other proteins, including those specifically mentioned above (ie Apo A-1, transferrin, lactoferrin, antibodies) and others.

Prior to crosslinking, the protein molecules are dispersed in the liquid medium, preferably at a concentration of at least 10 mg.mL$^{-1}$, or at least 20 mg.mL$^{-1}$, or at least 50 mg.mL$^{-1}$. The upper limit of the protein concentration may be determined by the solubility of the particular protein(s) being used, but the protein concentration may be 500 mg.mL$^{-1}$ or greater, or it may be up to 400 mg.mL$^{-1}$, 300 mg.mL$^{-1}$, or 200 mg.mL$^{-1}$. The concentration of protein is most commonly within the range of 8 mg.mL$^{-1}$ to 500 mg.mL$^{-1}$, more often 10 mg.mL$^{-1}$ to 200 mg.mL$^{-1}$, or 20 mg.mL$^{-1}$ to 200 mg.mL$^{-1}$, eg 50 mg.mL$^{-1}$ to 150 mg.mL$^{-1}$.

Nature of the Reaction Medium

The process of the invention is carried out in a suitable medium, which is most commonly an aqueous medium, preferably a buffer solution. One suitable buffer is phosphate buffered saline (PBS). Other conventional media may also be used.

The pH of the medium is preferably less than 10.0, or less than 9.0 or 8.0. The pH may be as low as 3.0 (or lower), but is more commonly above 4.0 or 5.0. Generally, the pH will be in the range 3.0 to 10.0, or 3.0 to 9.0, or 3.0 to 8.0. In many instances, the pH is in the range 3.0 to 8.5, more preferably 4.5 to 8.5, or 5.5 to 8.5, and particularly 5.5 to 7.5.

Nature of the Zero-length Crosslinker

A zero-length crosslinker is used to promote crosslinking between the proteinaceous molecules without the addition of other components in the crosslinked product, ie the particles do not contain a synthetic spacer, but instead comprise protein molecules that are coupled directly together. A variety of zero-length crosslinking chemistries or reagents may be used, and the following are provided as examples but are not intended to be exhaustive.

According to *Bioconjugate Techniques* (Hermanson G. T. (1996) *Academic Press*), two types of zero-length crosslinking chemistry applicable to proteins are:

a) a secondary or tertiary amine linkage made by the reductive amination of a primary or secondary amine with an aldehyde group; and
b) an amide linkage made by the condensation of a primary amine with a carboxylic acid.

The first of these could be applied to glycoproteins that possess carbohydrate chains containing cis-diols, which can be oxidised to form aldehyde groups, although this does not include albumin. The second type of crosslinking chemistry—amide linkages—should be applicable to all proteins, and hence is preferred in the present invention.

Three types of crosslinking reagent that can be used for formation of amide linkages are:

a) carbodiimides;
b) Woodward's reagent K (N-ethyl-3-phenylisoxazolium-3'-sulphonate); and
c) N,N-carbonyldiimidazole.

The use of carbodiimides is preferred in the present invention. There are a number of possible carbodiimides, for example EDC (1-ethyl-3-(3-dimethylaminopropyl)carbodiimide), CMC (1-cyclohexyl-3-(2-morpholinoethyl) carbodiimide), DCC (dicyclohexyl carbodiimide) and DIC (diisopropyl carbodiimide). However, DCC and DIC are not generally applicable to the crosslinking of proteins, due to poor solubility in water. The most preferred zero-length crosslinker for use in the present invention is EDC.

The concentration of zero-length crosslinker is preferably less than 500 mM, more preferably less than 200 mM, and may be less than 100 mM. The concentration of zero-length crosslinker is preferably above 5 mM, more preferably above 10 mM, and may be above 20 mM. The concentration of zero-length crosslinker is thus preferably in the range 5 mM, 10 mM or 20 mM to 100 mM, 200 mM or 500 mM, eg 5 mM to 500 mM or more preferably 20 mM to 200 mM.

In preferred embodiments in which the zero-length crosslinker is a carbodiimide, NHS(N-hydroxysuccinimide) or sulpho-NHS (N-hydroxysulphosuccinimide) may be added to the carbodiimide reaction to produce a more stable activated carboxyl intermediate and thus improve the yield of the reaction. The reaction is more efficient, so a lower concentration of zero-length crosslinker is required.

In embodiments of the invention in which NHS or sulpho-NHS is used, then the concentration of zero-length crosslinker is preferably less than 100 mM, more preferably less than 50 mM. The concentration of zero-length crosslinker is preferably above 2 mM, more preferably above 5 mM. The concentration of zero-length crosslinker is thus preferably in the range 2 mM or 5 mM to 50 mM or 100 mM, eg 2 mM to 100 mM, more preferably 5 mM to 50 mM. The concentration of the NHS or sulpho-NHS is preferably greater than 1 mM or 2 mM, and less than 50 mM or 20 mM. The concentration of NHS or sulpho-NHS is thus preferably in the range 1 mM or 2 mM to 20 mM or 50 mM, eg 1 mM to 50 mM, more preferably 2 mM to 20 mM.

EDC is the currently preferred zero-length crosslinker and, most preferably, EDC is used with NHS.

Reaction Conditions

The reaction temperature and reaction time are both variables that have an effect on the size of the resulting protein particles.

In practice, the temperature at which the reaction is carried out will be limited at the lower extreme by the need for the reaction medium to be liquid, ie by the freezing point of the medium, and at the upper extreme by the denaturation temperature of the protein. Where, as is usual, the reaction medium is aqueous, the reaction temperature is conveniently between 10° C. and 40° C. In the majority of cases, the reaction may be carried out at or close to the ambient room temperature, ie typically between 15° C. and 30° C., eg 20° C.+/−5° C.

The reaction time may be varied within quite wide ranges, but is typically from 1 hour to 4, 6, 8, 10 or 12 hours, eg about 2 hours.

The product may be purified following reaction of the protein molecules and zero-length crosslinker. Purification typically involves removal of the excess reagents, which may be carried out using any known method, eg column chromatography. A suitable chromatography medium is Sephadex G50.

It has been found that after the zero-length crosslinker has reacted with carboxyl groups in the protein molecule, the activated carboxyl may react with a free thiol group (as is present, for instance, in an albumin molecule) to form a thioester. As the thiol group may be useful as a means of reacting the protein molecule with, for instance, a therapeutic agent or imaging contrast agent, it is desirable for such a thioester to be hydrolysed. This may be achieved by heat treatment.

Heat treatment is preferably carried out at a temperature of between 20° C. and 50° C., for a period of from 1, 2, 4 or 8 hours, up to 10, 20, 30 or 40 hours. Generally, combinations of any of the reaction conditions and parameters given above may be used, the selection of the most appropriate or optimal conditions being determined by the precise nature of the materials used and the desired properties of the nanoparticles to be produced. However, in many embodiments, the reaction is carried out in an aqueous medium, at a pH in the range 3.0 to 8.5, eg 5.5 to 8.5 or 5.5 to 7.5, with a protein concentration of 8 mg.mL$^{-1}$ to 500 mg.mL$^{-1}$, eg 10 mg.mL$^{-1}$ to 200 mg.mL$^{-1}$, using a carbodiimide crosslinker, eg EDC, at a concentration of from 5 to 500 mM, eg between 20 and 200 mM. Where NHS or sulpho-NHS is used, the concentration of crosslinker may be lower, eg 2 mM to 100 mM, or 5 mM to 50 mM.

Coupling of Protein Particles to Contrast Agents or Therapeutic Agents

Coupling of an agent for delivery to the body to the protein particle may be carried out by any of a number of means, depending inter alia on the nature of the agent and the nature of the protein particle. In general, however, coupling will involve the formation of covalent bonds between the protein particle and the agent, or between the protein particle and a coupling moiety capable of forming a chemical or physical bond with the agent itself.

One preferred method of coupling, particularly appropriate to the coupling of metals, eg metals for use in MRI or nuclear imaging, or the coupling of radioactive metals for use in radiotherapy, involves the conjugation of the protein particle with a chelating agent which is capable of binding the metal.

In one particularly preferred embodiment, the chelating agent contains carboxyl groups, or derivatives thereof, that react with amine groups present in the protein particle to form amide bonds linking the chelating agent to the protein particle. A solution of a suitable salt of the metal may then be added, leading to chelation of the metal by the conjugated chelating agent.

Chelating agents that may be used include acetic acid derivatives of compounds containing multiple amine groups. Examples include ethylenediamine tetraacetic acid, diethylenetriamine pentaacetic acid, and derivatives thereof, eg diethylenetriamine pentaacetic acid anhydride. Other classes of chelating agent that may be useful include macrocyclic chelating agents. Examples of macrocyclic chelators are:

1,4,7-triazacyclononane-N,N',N''-triacetic acid (NOTA)
1,4,7,10-tetraazacyclododecane-N,N',N'',N'''-tetraacetic acid (DOTA)
1,4,8,11-tetraazacyclotetradecane-N,N',N'',N'''-tetraacetic acid (TETA)

Other methods for coupling chelating agents to the protein particle will be evident to those skilled in the art. Suitable chemistries most commonly involve the formation of linkages through amine, thiol, carbonyl, carboxyl or hydroxyl groups present in the protein particle and/or the chelating agent.

Where the agent is coupled to the protein particle in the form of a metal chelate, the chelate may be formed as part of the manufacturing process, or alternatively the metal may be added later, eg just prior to use. Particularly where the metal is a radioactive metal, it may be desirable for the metal ions to be added to the formulation immediately prior to use.

Likewise, organic agents, such as the iodine-containing compounds that are used as X-ray contrast agents may be coupled directly to the protein particle by the formation of covalent bonds between the organic agent and the protein particle. Methods for coupling organic agents to the protein particle will again be evident to those skilled in the art, and may involve the formation of linkages through amine, thiol, carbonyl, carboxyl or hydroxyl groups present in the protein particle and/or the organic agent.

Supply and Administration

The particles or conjugates according to the invention will generally be administered to the body as a formulation comprising a pharmaceutically acceptable medium. The medium is most commonly a liquid medium. Such formulations may be supplied to practitioners as a sterile, ready-to-use solution or else the particles or conjugates may be freeze-dried and then reconstituted before use with a suitable solution. For instance, the freeze-dried protein particles may be mixed with a solution of a radioactive label to produce the required formulation of conjugate in liquid medium prior to use.

The particles and formulations according to the invention may be administered by a variety of routes. The formulations may, for instance, be administered intravenously or by subcutaneous administration. The formulations may also be administered by oral or nasal inhalation, eg as a nebulised solution. Where appropriate, the formulations may be delivered direct to a disease site via a catheter. For other applications the formulations may be delivered topically, eg by application to the skin. In such cases, the formulations may be applied as creams or ointments, or may be incorporated into patches that are applied to the skin.

Examples of applications of the nanoparticles according to the invention include the following.

The particles may be of value in enhancing the delivery of drugs across membranes (eg lung, nasal, buccal etc). In particular, nanoparticles, eg of rHA, can be transported across membranes by transcytosis. It is known that particulate forms of proteins are more readily taken up by, and/or transported across membranes, than single molecules. Also, nanoparticles can be prepared with charged or hydrophilic groups attached to them (chemically) to enhance uptake.

The particles may also be used for gene delivery. For instance, DNA can be linked to the particles by chemical means, to enable the DNA to travel across the cell membrane and the nuclear envelope.

The particles may also be used to enhanced responses to vaccines, by virtue of the particles being made from vaccine molecules, or by linking antigen to particles made of, for instance, rHA.

Use of the particles may also increase drug uptake into tumours. For instance, tumour cells are known to over-express gp60/SPARK and may show enhanced uptake of rHA nanoparticles. This may also provide a mechanism for overcoming multi-drug resistance (by stopping drugs being pumped directly out of the tumour cells).

Particles according to the invention may also be useful in the delivery of drugs or other useful agents to wounds.

Topical delivery of the particles according to the invention may have the beneficial effect of retaining drugs or other actives on the surface of the skin, especially in pores etc. Again, the preparation of particles with surface charge may enhance skin adhesion The particles may also be used for oral drug delivery, as they may be used to deliver molecules across the gut wall or across the Payers patch.

The particles according to the invention may also find application in non-pharmaceutical settings, eg in personal care products. Other, industrial applications are also envisaged, eg for the delivery of enzymes in industrial processes.

EXEMPLARY EMBODIMENTS OF THE INVENTION

Currently preferred embodiments of the invention will now be described in greater detail, by way of illustration only, with reference to the following Examples and the accompanying Figures, in which FIG. 1 shows gel permeation HPLC results obtained for the products of Example 1.

GENERAL METHODS

Crosslinking of rHA to Form Protein Particles

Formulated rHA (approximately 20% (w/v) rHA, 32 mM octanoate, 145 mM Na$^+$, 15 mg.L$^{-1}$ Polysorbate 80, pH7.0) was diluted to the indicated rHA concentration with the indicated buffer. EDC or EDC+NHS was added at the indicated concentrations, and the sample mixed and incubated at room temperature (approximately 20° C.) for the indicated time.

Desalting

To remove excess reactants, crosslinked rHA was desalted by Sephadex chromatography. Unless otherwise indicated, desalting was performed in phosphate buffered saline (PBS) containing 0.9% (w/v) NaCl, 15 mM Na$_2$HPO$_4$, 5 mM NaH$_2$PO$_4$.

Heat Treatment

Where indicated, crosslinked rHA was heat-treated by incubation at approximately 45° C. for the indicated time, followed, where indicated, by a repeat desalting step.

Gel Permeation HPLC (GPHPLC)

GPHPLC used a TSKgel G3000$_{SWXL}$ 0.78×30 cm analytical column and guard run at 1 mL.min$^{-1}$ in PBS, with effluent monitoring at 280 nm. Samples were diluted appropriately in PBS and 10-25 µL injected.

Native PAGE

Native PAGE was performed using Novex 4-12% Tris Glycine gels (Invitrogen Ltd., 3 Fountain Drive, Inchinnan Business Park, Paisley PA4 9RF, United Kingdom) according to the manufacturer's instructions, with samples diluted appropriately in PBS. Gels were stained with GelCode Blue (Pierce Biotechnology, Inc, 3747 N Meridian Rd, PO Box 117, Rockford, Ill. 61105, USA) according to the manufacturer's instructions.

Free Thiol Assay

Blank and sample were made to 1 mL with 0.1M TrisHCl, 0.01M EDTA pH8 and A$_{412}$ measured. 50 µL 0.01M 5,5'-dithiobis-(2-nitrobenzoic acid) in 0.05M sodium phosphate pH7 was added and A$_{412}$ remeasured after 10 min at room temperature. The thiol content was calculated using $\epsilon_{412}=13600M^{-1}$ cm$^{-1}$.

Particle Size Determination

Samples were diluted to 1-5 mg.mL$^{-1}$ rHA with PBS and 0.2 µm filtered prior to triplicate analysis using a Malvern Zetasizer Nano S with low volume disposable cuvette. The mean particle size based on scattered light intensity and the standard deviation of the size distribution were determined using Malvern Dispersion Technology Software v4.10.

Bound Methotrexate Assay

Following desalting and appropriate dilution of the sample in PBS, protein-bound methotrexate (MTX) concentration was determined by A$_{373}$ measurement, in comparison with MTX solutions of known concentration.

EXAMPLE 1

Figure 1:
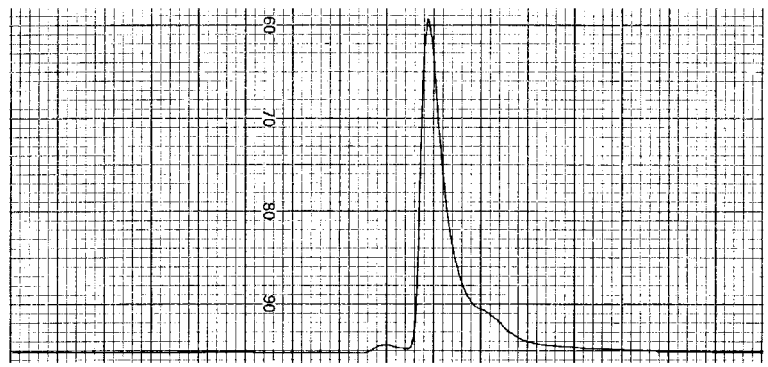
Figure 1:
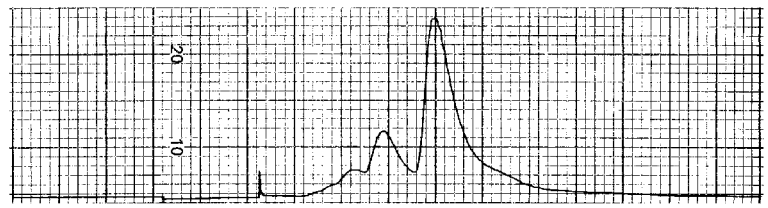
Figure 1:
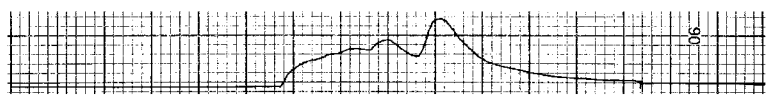
Figure 1:

Crosslinking of rHA and Analysis by GPHPLC: Influence of Crosslinker Concentration Crosslinking was performed at 100 mg.mL$^{-1}$ rHA diluted in PBS with 0, 15, 30 and 45 mM EDC, 15 mM EDC+5 mM NHS and a 2 h reaction time. Products were analysed by GPHPLC as shown in FIG. 1.

The chromatograms show the elution of monomeric rHA starting material (FIG. 1a), and gradually increasing amounts of larger species (protein particles) with increasing concentrations of EDC and addition of NHS.

NB The broad peak eluting at the start of chromatogram c occurs before the void volume of the column and hence is a baseline artefact, not related to the sample.

EXAMPLE 2

Figure 2:
FIG. 2 shows gel permeation HPLC results obtained for the products of Example 2.
Figure 2:
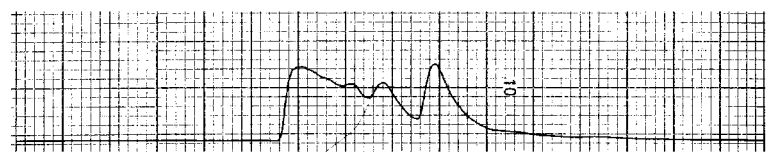
Figure 2:
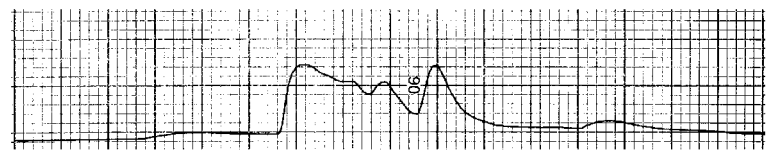
Figure 2:
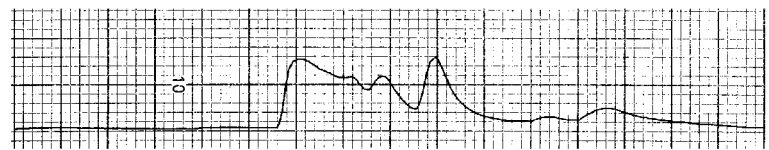

Crosslinking of rHA and Analysis by GPHPLC: Effect of Post-Crosslinking Treatments Crosslinking was performed at 100 mg.mL$^{-1}$ rHA diluted in PBS with 15 mM EDC+5 mM NHS and a 2 h reaction time. The crosslinked product (containing protein particles) was desalted in water, formulated by the addition of $SnCl_2$, $Na_2HPO_4$, glucose and Pluronic F68 and freeze-dried. The product at each stage was analysed by GPHPLC, and the results are shown in FIG. 2, which indicates that desalting, formulation and freeze-drying has no significant effect on the protein particles.

EXAMPLE 3

Crosslinking of rHA and Analysis by Native PAGE

Figure 3:
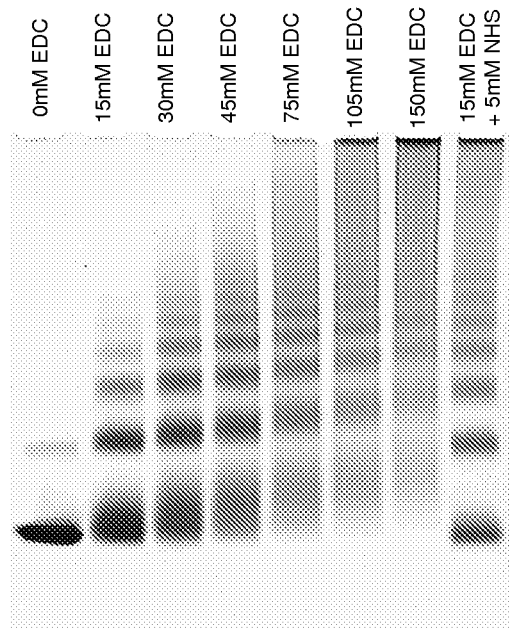
FIG. 3 shows native PAGE results for the products of Example 3.

Crosslinking was performed at 100 mg.mL$^{-1}$ rHA diluted in PBS with 0, 15, 30, 45, 75, 105 and 150 mM EDC, 15 mM EDC+5 mM NHS and a 2 h reaction time. Products were analysed by native PAGE, and the results are shown in FIG. 3.

The results are consistent with the GPHPLC results discussed above, in that they show the formation of increased quantities of less mobile species (protein particles) with increasing concentrations of EDC and incorporation of NHS.

EXAMPLE 4

Crosslinking of rHA and Determination of Free Thiol Content of Product

Crosslinking was performed at 100 mg.mL$^{-1}$ rHA diluted in PBS with 15 mM EDC+5 mM NHS and a 2 h reaction time. The crosslinked product, desalted in water, showed a free thiol level of 0.04 mol.mol$^{-1}$, compared to 0.64 mol.mol$^{-1}$ for the starting rHA.

EXAMPLE 5

Figure 4:
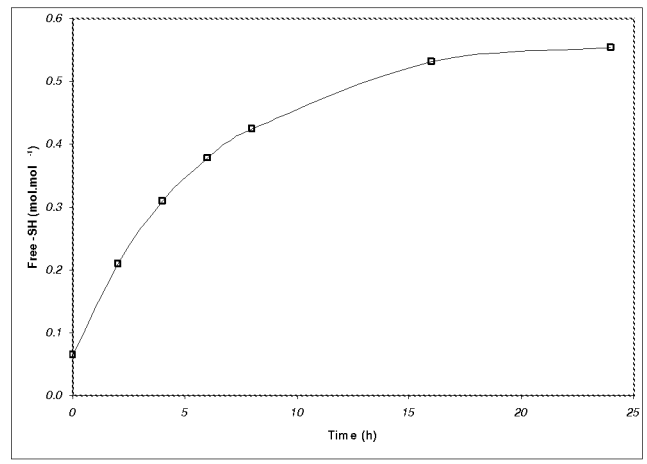
FIG. 4 shows the increase in free thiol groups during heat treatment of the crosslinked product detailed in Example 5.

Crosslinking of rHA: Dependence of Free Thiol Content of Product on Duration of Heat Treatment Crosslinking was performed at 100 mg.mL$^{-1}$ rHA diluted in PBS with 15 mM EDC+5 mM NHS and a 2 h reaction time. The crosslinked product was desalted and heat treated for the indicated times, with aliquots taken for free thiol assay. The results are shown in FIG. 4. As can be seen, the free thiol content returned substantially to that of the rHA starting material for heat treatment times of 16 hours and longer.

EXAMPLE 6

Effect of Variation in Reaction Conditions
a) [EDC], [NHS] and Time

Figure 5:
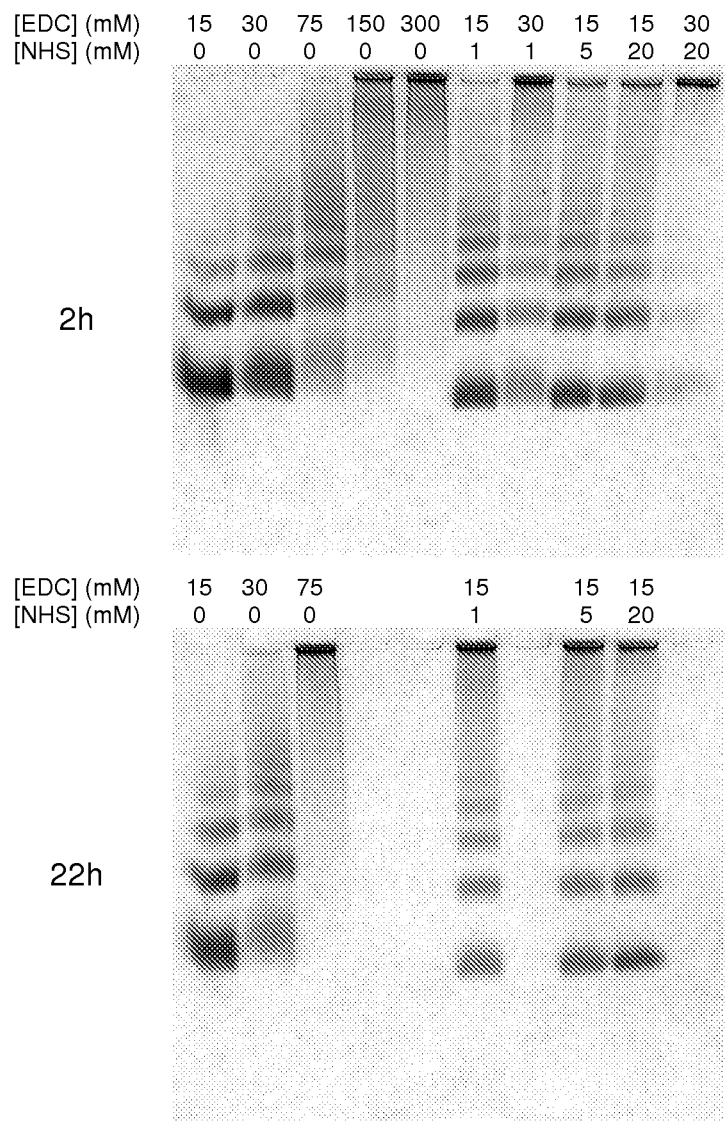
FIG. 5 shows native PAGE results for the products of Example 6(a).
Figure 6:
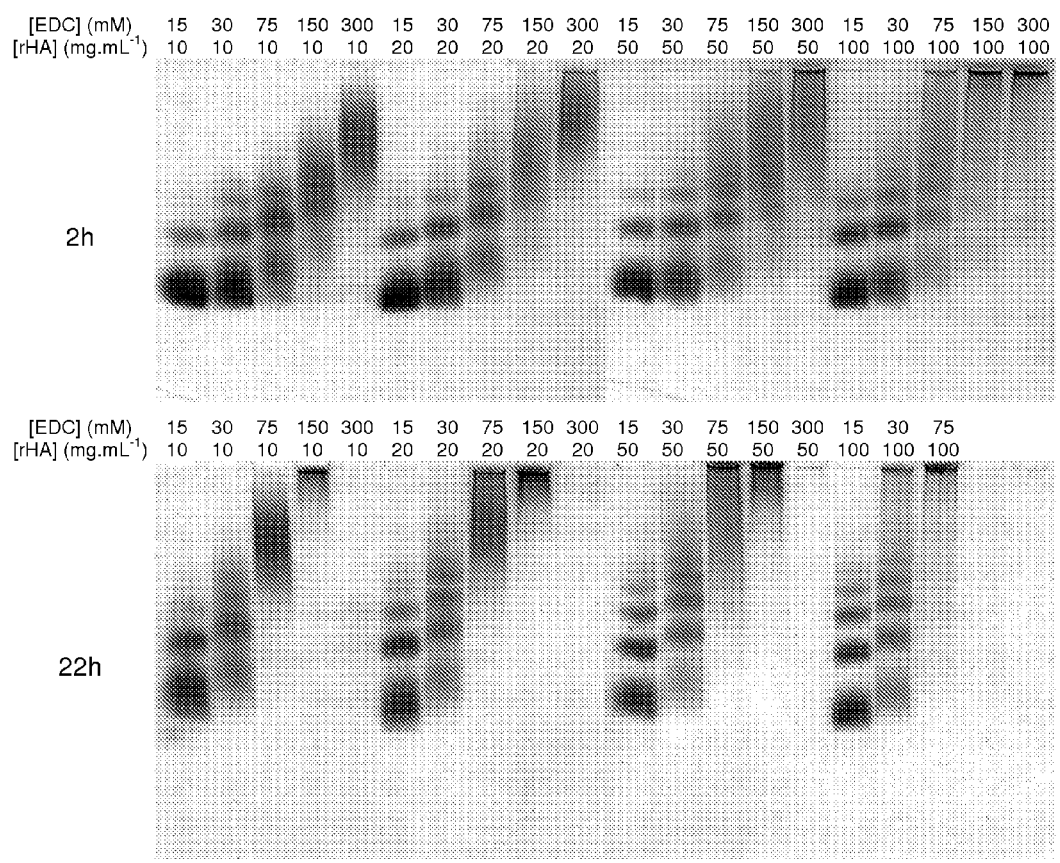
FIG. 6 shows native PAGE results for the products of Example 6(b).
Figure 7:
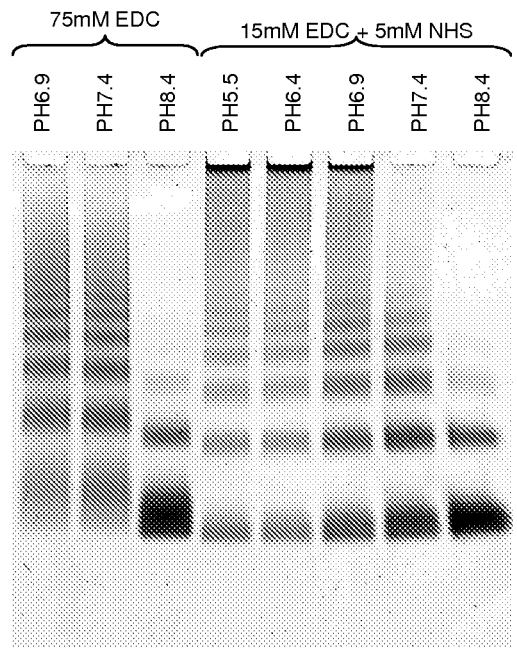
FIG. 7 shows native PAGE results for the products of Example 6(c).

Crosslinking was performed at 100 mg.mL$^{-1}$ rHA diluted in PBS with EDC concentrations of 15, 30, 75, 150 and 300 mM, each at 0, 1, 5 and 20 mM NHS. All samples that had not formed a gel were analysed by native PAGE after 2 and 22 h reaction times—see FIG. 5, which indicates that somewhat greater quantities of protein particles were formed after the longer reaction time.
b) [EDC], [rHA] and Time Crosslinking was performed at 10, 20, 50 and 100 mg.mL$^{-1}$ rHA diluted in PBS, each with EDC concentrations of 15, 30, 75, 150 and 300 mM. All samples that had not formed a gel were analysed by native PAGE after 2 and 22 h reaction times—see FIG. 6.
c) pH 100 mg.mL$^{-1}$ rHA was prepared by dilution in either 0.9% (w/v) NaCl, 20 mM MES or 0.9% (w/v) NaCl, 20 mM EPPS or PBS. Aliquots of the MES sample were adjusted to approximately pH5.5 and pH6.5. Aliquots of the EPPS sample were adjusted to approximately pH7.5 and pH8.5. The actual starting pH was measured prior to crosslinking of each sample with 75 mM EDC and 15 mM EDC+5 mM NHS and a 2 h reaction time. All samples that had not formed a gel were analysed by native PAGE—see FIG. 7. The results indicate that cross-linking was more efficient at pH values below 7.

EXAMPLE 7

Comparison of Results Obtained Using NHS Plus EDC and EDC Alone

Figure 8:
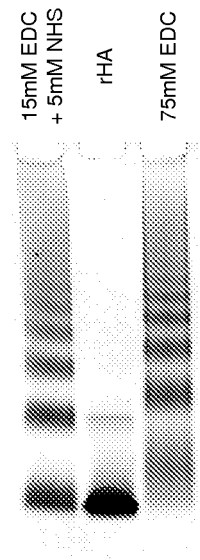
FIG. 8 shows the native PAGE results for desalted products of Example 7.
Figure 9:
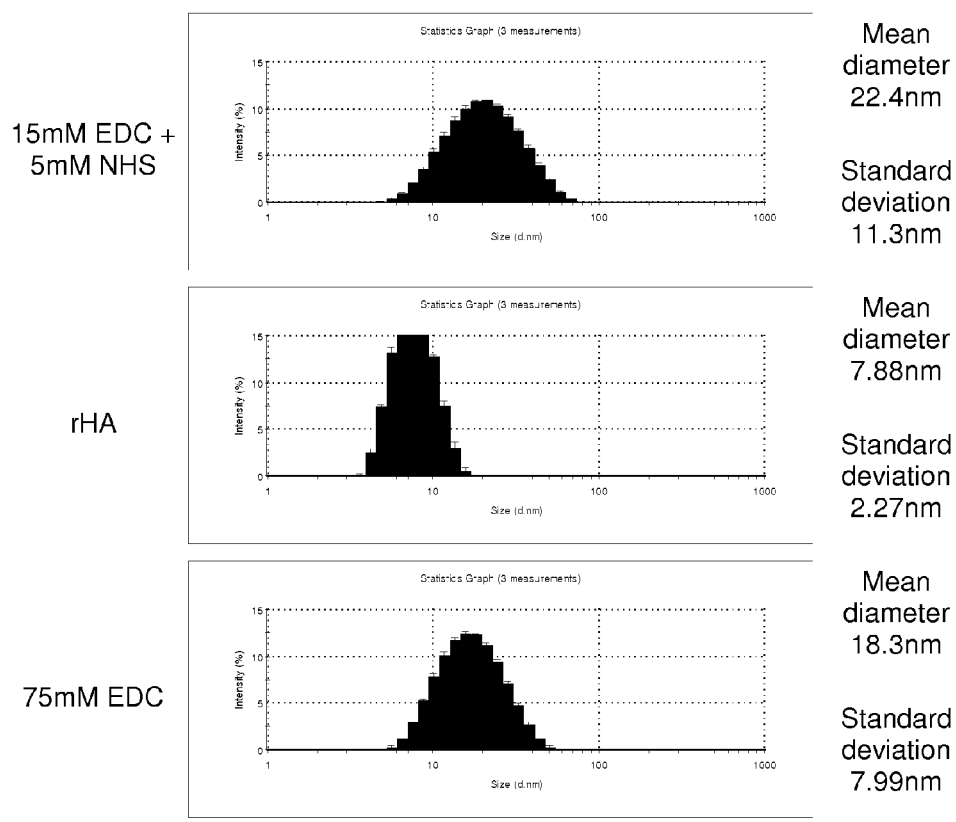
FIG. 9 shows particle size distributions determined by light scattering for the desalted products of Example 7.

Crosslinking was performed at 100 mg.mL$^{-1}$ rHA diluted in PBS with 15 mM EDC+5 mM NHS and 75 mM EDC and a 2 h reaction time. After desalting, the crosslinked products were analysed by native PAGE and light scattering, in comparison with the rHA starting material. The native PAGE results are shown in FIG. 8 and the particle size distributions determined by light scattering analysis are shown in FIG. 9. The results indicate that the use of 5 mM NHS with only 15 mM EDC yielded a comparable result to the use of 75 mM EDC alone.

EXAMPLE 8

Further Comparison of Results Obtained Using NHS Plus EDC and EDC Alone

Crosslinking was performed at 100 mg.mL$^{-1}$ rHA diluted in PBS with 15 mM EDC+5 mM NHS and 75 mM EDC and a 2 h reaction time. The crosslinked product was desalted, heat treated and desalted again. The free thiol level increased on heat treatment from 0.03 to 0.54 mol.mol$^{-1}$ for the EDC+NHS product and from 0.02 to 0.50 mol.mol$^{-1}$ for the EDC product. The desalted products pre- and post-heat treatment were analysed by native PAGE, GPHPLC and light scattering, in comparison with the rHA starting material.

Figure 10:
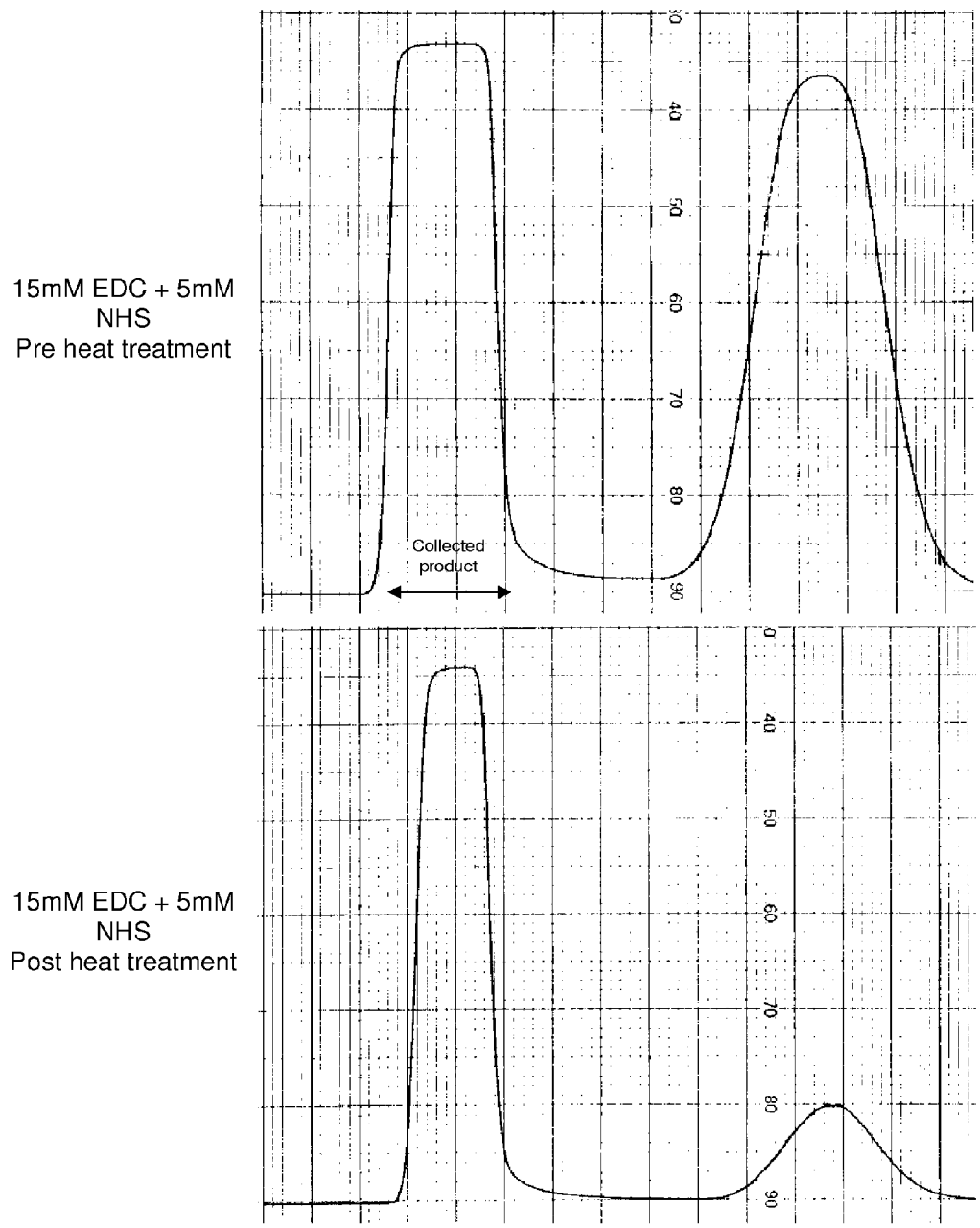
FIG. 10 shows desalting chromatograms for the products of Example 8.

FIG. 10 shows the desalting chromatograms. The desalting was monitored at 260 nm. The upper chromatogram in FIG. 10 was obtained prior to heat treatment. The left-hand peak corresponds to the product that was collected and then heat-treated; the right-hand peak corresponds to free NHS. The lower chromatogram indicates that, after heat treatment, further free NHS has been generated. These results show that NHS was released from the collected product by the heat treatment process. The same effect was shown with the EDC-only reaction (data not shown).

Figure 11:
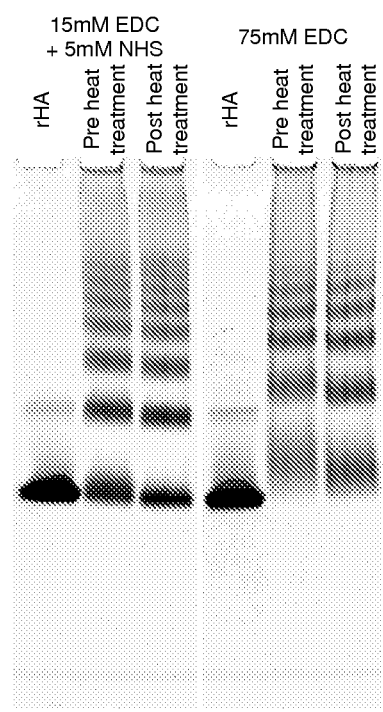
FIG. 11 shows native PAGE results for the products of Example 8.
Figure 12:
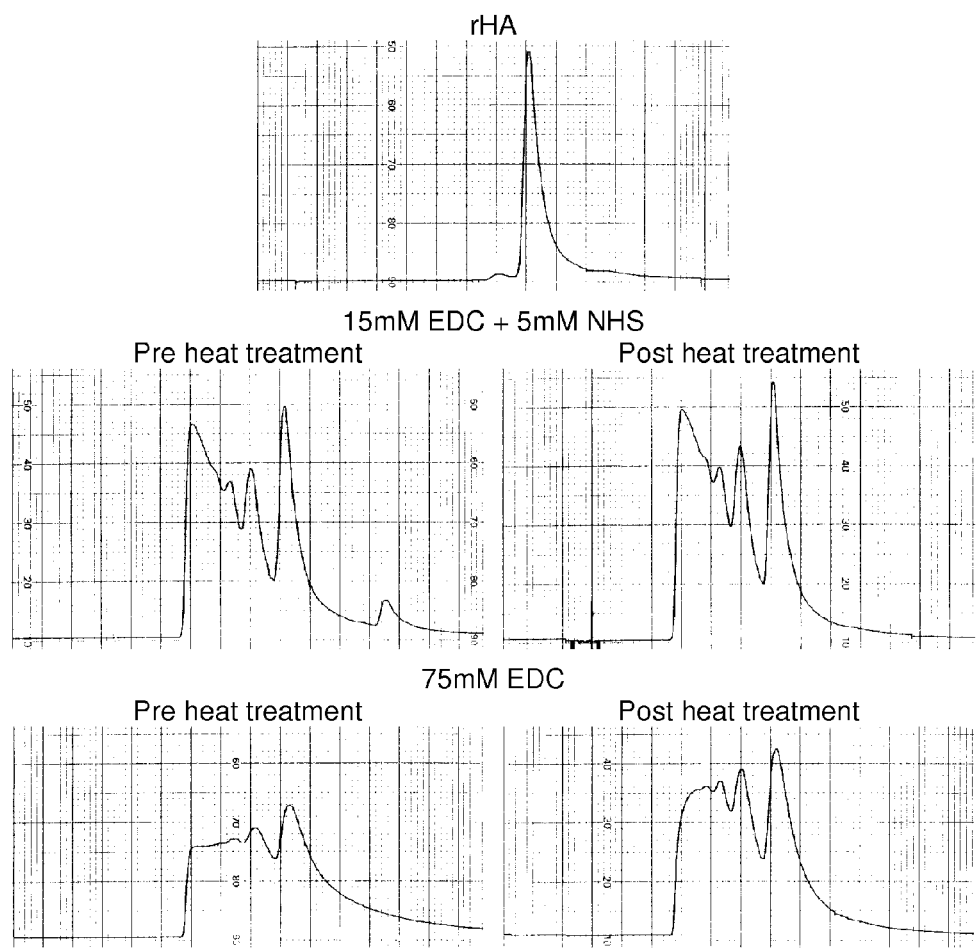
FIG. 12 shows gel permeation HPLC results for the products of Example 8.
Figure 13:
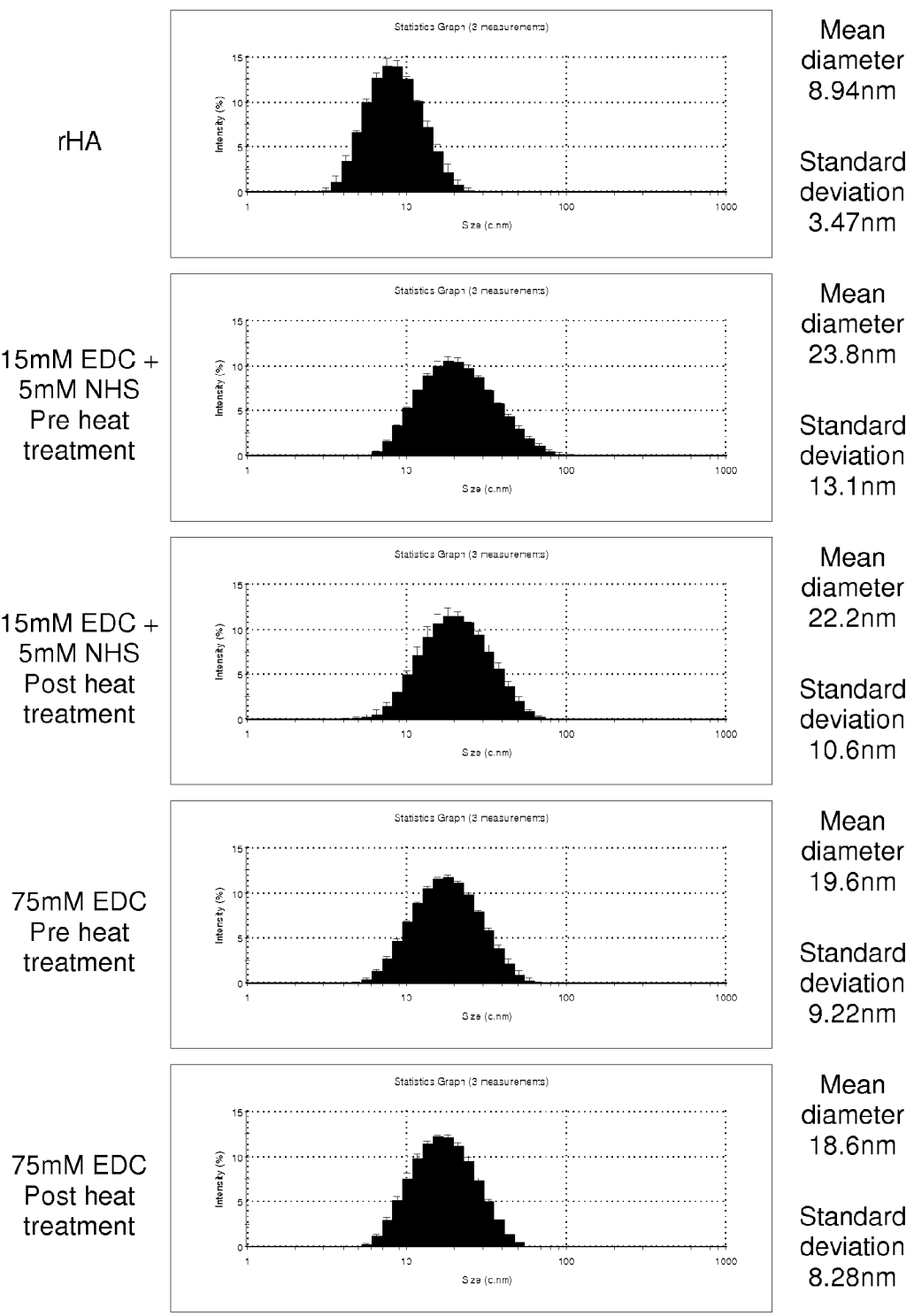
FIG. 13 shows particle size distributions determined by light scattering for the products of Example 8.

FIG. 11 shows the native PAGE results, FIG. 12 shows results obtained by GPHPLC and FIG. 13 shows particle size data obtained by light scattering. The data show that the heat treatment step has no significant effect on the protein particles, save perhaps for a very slight reduction in mean particle size (FIG. 13) and increase in mobility (FIG. 11).

EXAMPLE 9

Effect of Varying [rHA] and [EDC] at Constant [NHS]

Crosslinking was performed at 20, 50 and 100 mg.mL$^{-1}$ rHA diluted in PBS each with 10 mM EDC+5 mM NHS, 15 mM EDC+5 mM NHS, 25 mM EDC+5 mM NHS and 50 mM EDC+5 mM NHS and a 2 h reaction time. All samples that had not formed a gel were desalted, heat treated and desalted again. The particle size distributions of the products were analysed by light scattering. The results are given in Table I.

TABLE I

| | [rHA]/mg·mL$^{-1}$ | | | | | |
| --- | --- | --- | --- | --- | --- | --- |
| | 20 | | 50 | | 100 | |
| [EDC]/mM | Mean diameter/nm | Standard deviation/nm | Mean diameter/nm | Standard deviation/nm | Mean diameter/nm | Standard deviation/nm |
| 10 | 11.0 | 4.26 | 12.8 | 5.28 | 15.3 | 7.11 |
| 15 | 12.1 | 4.66 | 15.7 | 7.18 | 20.6 | 9.74 |
| 25 | 15.1 | 6.43 | 25.3 | 13.3 | 48.3 | 24.2 |
| 50 | 25.4 | 12.6 | 73.9 | 35.0 | not meas. | not meas. |

By comparison, the rHA starting material had a mean diameter of 8.38 nm and a standard deviation of 2.99 nm.

EXAMPLE 10

Effect of Varying [EDC] and [NHS] at Constant [rHA]

Crosslinking was performed at 100 mg.mL$^{-1}$ rHA diluted in PBS with 15, 25 and 35 mM EDC each with 2, 5, 10 and 20 mM NHS and a 2 h reaction time. All samples that had not formed a gel were desalted, heat treated and desalted again. The particle size distributions of the products were analysed by light scattering. The results are shown in Table II.

TABLE II

| | [EDC]/mM | | | | | |
| --- | --- | --- | --- | --- | --- | --- |
| | 15 | | 25 | | 35 | |
| [NHS]/mM | Mean diameter/nm | Standard deviation/nm | Mean diameter/nm | Standard deviation/nm | Mean diameter/nm | Standard deviation/nm |
| 2 | 18.7 | 8.93 | 59.5 | 39.7 | 73.2 | 35.4 |
| 5 | 23.1 | 12.4 | 48.6 | 25.7 | 117 | 67.2 |
| 10 | 27.7 | 16.3 | 72.9 | 38.3 | not meas. | not meas. |
| 20 | 23.3 | 12.2 | 66.3 | 32.4 | not meas. | not meas. |

By comparison, the rHA starting material had a mean diameter of 8.39 nm and a standard deviation of 2.96 nm.

EXAMPLE 11

Crosslinking of Recombinant Transferrin

Recombinant transferrin (rTF) was crosslinked using the same methods as described for rHA. Crosslinking was performed at 100 mg.mL$^{-1}$ rTF diluted in PBS with 15, 25 and 35 mM EDC each with 5 mM NHS and 1, 2 or 4 h reaction times. All samples that had not formed a gel were desalted and analysed by light scattering. The results are shown in Table III:

TABLE III

| | Reaction time/h | | | | | |
| --- | --- | --- | --- | --- | --- | --- |
| | 1 | | 2 | | 4 | |
| [EDC]/mM | Mean diameter/nm | Standard deviation/nm | Mean diameter/nm | Standard deviation/nm | Mean diameter/nm | Standard deviation/nm |
| 15 | 17.0 | 7.7 | 34.3 | 26.0 | 57.5 | 32.4 |
| 25 | 31.0 | 18.4 | 99.7 | 53.1 | not meas. | not meas. |
| 35 | 55.6 | 31.9 | not meas. | not meas. | not meas. | not meas. |

By comparison, the rTF starting material had a mean diameter of 7.78 nm and a standard deviation of 1.80 nm.

EXAMPLE 12

Crosslinking of Apolipoprotein A-1

Apolipoprotein A-1 (Apo A-1) was crosslinked using 50 mg.mL$^{-1}$ Apo A-1 in PBS with 25 mM EDC and 5 mM NHS for 1, 2 and 4 h reaction times. All samples were desalted and analysed by light scattering, in comparison with the starting Apo A-1. The results are shown in Table IV:

TABLE IV

| Reaction time/h | Mean diameter/nm | Standard deviation/nm |
| --- | --- | --- |
| 1 | 21.8 | 10.8 |
| 2 | 44.9 | 33.7 |
| 4 | 57.6 | 33.4 |

By comparison, the Apo A-1 starting material had a mean diameter of 12.5 nm and a standard deviation of 5.72 nm.

EXAMPLE 13

Preparation of Crosslinked rHA Particles Containing a Therapeutic Agent (Methotrexate)

Crosslinking of rHA in the presence of methotrexate (MTX) was performed at 100 mg.mL$^{-1}$ rHA diluted in PBS, with 25 mM EDC+5 mM NHS, 9.8 mM MTX (6.5 mol.mol$^{-1}$ rHA) and a 2h reaction time. The crosslinked product was desalted, assayed for protein-bound MTX and analysed by light scattering, in comparison with the starting rHA. The product contained bound MTX at a concentration of 2.3 mol.mol$^{-1}$ rHA and had a mean diameter of 37.9 nm and a standard deviation of 22.6 nm. By comparison, the rHA starting material had a mean diameter of 8.24 nm and a standard deviation of 2.44 nm.

EXAMPLE 14

Coupling of a Therapeutic Agent (Methotrexate) to Crosslinked rHA Particles

Crosslinking of rHA was performed at 100 mg.mL$^{-1}$ rHA diluted in PBS, with 25 mM EDC+5 mM NHS and a 2 h reaction time. The crosslinked product was desalted, heat-treated for 22 h, desalted again and concentrated to 20 mg.mL$^1$ rHA by ultrafiltration.

NHS-activated MTX was prepared by reacting 10 mM MTX with 20 mM NHS and 100 mM EDC in PBS for 1 h at room temperature, maintaining approximately pH7 by appropriate addition of NaOH and HCl. The final NHS-activated MTX concentration was 9.8 mM.

MTX coupling to cross-linked rHA was performed by mixing equal volumes of 20 mg.mL$^{-1}$ crosslinked rHA and 9.8 mM NHS-activated MTX (33 mol.mol$^{-1}$ rHA). Samples were taken after 1½ h and 3 h reaction at room temperature, desalted and assayed for protein-bound MTX. All cross-linked rHA samples were also analysed by light scattering, in comparison with the starting rHA. The results are shown in Table V:

TABLE V

| Sample | Reaction time/ h | Protein-bound MTX/ mol · mol$^{-1}$ rHA | Mean diameter/ nm | Standard deviation/ nm |
|---|---|---|---|---|
| Crosslinked rHA | — | — | 48.7 | 23.4 |
| MTX-labelled crosslinked rHA | 1½ | 12.6 | 54.2 | 26.0 |
|  | 3 | 14.4 | 58.4 | 29.5 |

By comparison, the rHA starting material had a mean diameter of 8.09 nm and a standard deviation of 2.47 nm.

EXAMPLE 15

Coupling of a Contrast Agent (Cadmium Chelate) to Crosslinked rHA Particles

Diethylenetriaminepentaacetic acid (DTPA) coupling to cross-linked rHA was performed by adding 0.4 g DTPA anhydride to 6 mL 20 mg.mL$^{-1}$ crosslinked rHA (as for Example 14) over a period of 30 min with constant stirring, maintaining approximately pH8 by addition of 5M NaOH. Stirring was continued for 30 min after the final addition, the sample adjusted to pH7 with 3M HCl and desalted in 0.9% (w/v) NaCl.

The protein-bound DTPA groups were titrated with 0.1M GdCl$_3$ in the presence of xylenol orange indicator, maintaining pH5.5-6.0 by addition of 1M NaOH. The bound DTPA level was 43 mol.mol$^{-1}$ rHA. All cross-linked rHA samples were also analysed by light scattering, in comparison with the starting rHA. The results are shown in Table VI:

TABLE VI

| Sample | Mean diameter/ nm | Standard deviation/ nm |
|---|---|---|
| Crosslinked rHA | 48.1 | 23.8 |
| DTPA-labelled crosslinked rHA | 67.6 | 36.9 |
| DTPA-Gd-labelled crosslinked rHA | 62.4 | 31.8 |

By comparison, the rHA starting material had a mean diameter of 7.77 nm and a standard deviation of 2.15 nm.

EXAMPLE 16

Crosslinking of rHA Using Woodward's Reagent K

Crosslinking with Woodward's reagent K (WRK) was performed at 100 mg.mL$^{-1}$ rHA diluted in PBS, with 0.1M WRK and a 30 min reaction time. The crosslinked product was diluted in PBS and analysed by light scattering, in comparison with the starting rHA. The product had a mean diameter of 13.5 nm and a standard deviation of 5.76 nm. By comparison, the rHA starting material had a mean diameter of 8.42 nm and a standard deviation of 2.87 nm.

EXAMPLE 17

Crosslinking of rHA Using N,N-carbonvidiimidazole

Crosslinking with N,N-carbonyldiimidazole (CDI) was performed at 100 mg.mL$^1$ rHA diluted in PBS, with 0.5M CDI. The reaction was allowed to go to completion. The crosslinked product was diluted in PBS and analysed by light scattering, in comparison with the starting rHA. The product had a mean diameter of 50.7 nm and a standard deviation of 26.0 nm. By comparison, the rHA starting material had a mean diameter of 8.42 nm and a standard deviation of 2.87 nm.

The invention claimed is:

1. A process for the preparation of protein particles, which process comprises:
   causing or allowing protein molecules dispersed in a liquid medium at a concentration of 8 mg.mL$^{-1}$ or greater to react in the presence of a zero-length crosslinker, so as to produce protein particles comprising protein molecules that are covalently bonded together, wherein the protein particles have a mean particle size of from 5 nm to 200 nm, and wherein the protein particles are substantially free of material other than the protein molecules from which the article is formed and any therapeutic or other agents to which the particles are physically or chemically bound.

2. The process of claim 1, wherein the protein molecules are albumin molecules.

3. The process of claim 1, wherein the protein molecules are selected from the group consisting of collagen, elastin, keratin, fibroin, fibrin, fibronectin, transthyretin, fibrinogen, thrombin, transferrin, apolipoprotein A-1, lactoferrin, antibodies and fusion proteins.

4. A process as claimed in claim 3, wherein the protein molecules are transferrin molecules.

5. A process as claimed in claim 3, wherein the protein molecules are apolipoprotein A-1 molecules.

6. A process as claimed in claim 3, wherein the protein molecules are lactoferrin molecules.

7. A process as claimed in claim 3, wherein the protein molecules are antibodies.

8. A process as claimed in claim 3, wherein the protein molecules are fusion proteins.

9. A process as claimed in claim 8, wherein the fusion proteins are fusions of human serum albumin and another protein or polypeptide.

10. The process of claim 1, wherein the protein molecules are recombinant products.

11. The process of claim 10, wherein the protein molecules are recombinant human serum albumin molecules.

12. The process of claim 1, wherein the concentration of protein is in the range 8 mg.mL$^{-1}$ to 500 mg.mL$^{-1}$.

13. The process of claim 1, wherein the crosslinker is selected from the group consisting of carbodiimides, Woodward's agent K, and N,N-carbonyldiimidazole.

14. The process of claim 13, wherein the zero-length crosslinker is a carbodiimide.

15. The process of claim 14, wherein the carbodiimide is 1-ethyl-3-(3-dimethylaminopropyl)carbodiimide.

16. The process of claim 13, wherein the concentration of crosslinker is in the range 5 mM to 500 mM.

17. A process as claimed in claim 14, wherein the reaction is carried out in the presence of N-hydroxysuccinimide or N-hydroxysulphosuccinimide.

18. A process as claimed in claim 17, wherein the concentration of crosslinker is 2 mM to 100 mM.

19. A process as claimed in claim 17, wherein the concentration of N-hydroxysuccinimide or N-hydroxysulphosuccinimide is 1 mM to 50 mM.

20. The process of claim 1, wherein the liquid medium is aqueous.

21. The process of claim 20, wherein the aqueous liquid medium is a buffer solution.

22. The process of claim 20, wherein the pH of the medium is in the range 3.0 to 8.5.

23. The process of claim 1, wherein the concentration of protein is in the range 8 mg.mL$^{-1}$ to 500 mg.mL$^{-1}$.

24. The process of claim 1, wherein the concentration of protein is in the range 10 mg.mL$^{-1}$ to 200 mg.mL$^{-1}$.

25. The process of claim 1, wherein the concentration of protein is in the range 20 mg.mL$^{-1}$ to 200 mg.mL$^{-1}$.

26. The process of claim 1, wherein the concentration of protein is in the range 50 mg.mL$^{-1}$ to 150 mg.mL$^{-1}$.

27. A process as claimed in claim 17, wherein the concentration of crosslinker is 5 mM to 50 mM.

28. A process as claimed in claim 17, wherein the concentration of N-hydroxysuccinimide or N-hydroxysulphosuccinimide is 2 mM to 20 mM.

29. The process of claim 20, wherein the pH of the medium is in the range 4.5 to 8.5.

30. The process of claim 20, wherein the pH of the medium is in the range 5.5 to 8.5.

31. The process of claim 20, wherein the pH of the medium is in the range 5.5 to 7.5.

32. The process of claim 13, wherein the concentration of crosslinker is in the range 20 mM to 200 mM.

33. A process for the preparation of protein particles, which process comprises:
   causing protein molecules dispersed in a liquid medium at a concentration of 8 mg.mL–1 or greater to react in the presence of a zero-length crosslinker, so as to produce protein particles comprising protein molecules that are covalently bonded together, wherein the protein particles have a mean particle size of from 5 nm to 200 nm, and wherein the particles are substantially free of material other than the protein molecules from which the particle is formed.

* * * * *